(12) United States Patent
Kong et al.

(10) Patent No.: US 6,759,857 B2
(45) Date of Patent: Jul. 6, 2004

(54) METHOD AND APPARATUS FOR IDENTIFYING HIGH METAL CONTENT ON A SEMICONDUCTOR SURFACE

(75) Inventors: Sik On Kong, Singapore (SG); Tsui Ping Chu, Singapore (SG)

(73) Assignee: Chartered Semiconductor Manufacturing Ltd., Singapore (SG)

( * ) Notice: Subject to any disclaimer, the term of this patent is extended or adjusted under 35 U.S.C. 154(b) by 0 days.

(21) Appl. No.: 10/256,408

(22) Filed: Sep. 27, 2002

(65) Prior Publication Data

US 2003/0042915 A1 Mar. 6, 2003

Related U.S. Application Data

(62) Division of application No. 09/290,919, filed on Apr. 12, 1999, now Pat. No. 6,476,604.

(51) Int. Cl.[7] .................. G01R 31/305; G01N 21/55
(52) U.S. Cl. .................. 324/752; 324/750; 324/765; 438/7
(58) Field of Search .................. 324/752, 765; 216/85; 356/371, 372, 376, 394; 427/8; 438/7–9

(56) References Cited

U.S. PATENT DOCUMENTS

| | | | |
|---|---|---|---|
| 5,364,510 A | 11/1994 | Carpio | 204/153.1 |
| 5,552,327 A | 9/1996 | Bachmann et al. | 437/8 |
| 5,683,180 A | 11/1997 | De Lyon et al. | 374/161 |
| 5,820,689 A | 10/1998 | Tseng et al. | 134/3 |
| 5,840,368 A | 11/1998 | Ohmi | 427/255.4 |
| 6,010,538 A | * 1/2000 | Sun et al. | |
| 6,108,093 A | * 8/2000 | Berman | 356/394 |
| 6,110,752 A | * 8/2000 | Litvak | 438/8 |

* cited by examiner

*Primary Examiner*—N. Le
*Assistant Examiner*—Darrell Kinder
(74) *Attorney, Agent, or Firm*—George O. Saile; Rosemary L. S. Pike

(57) ABSTRACT

A new method and apparatus for detecting and measuring the level of metal present on the surface of a substrate is achieved. Energy, in the form of rf or light or microwave energy, is directed at the surface of a wafer, the reflected energy or the energy that passes through the semiconductor substrate is captured and analyzed for energy level and/or frequency content. Based on this analysis conclusions can be drawn regarding presence and type of metal on the surface of the wafer. Furthermore, by inclusion of metal within the resonating circuit of an rf generator changes the frequency of the vibration and therefore detects the presence of metal.

14 Claims, 4 Drawing Sheets

METHOD AND APPARATUS FOR IDENTIFYING HIGH METAL CONTENT ON A SEMICONDUCTOR SURFACE

This is a division of patent application Ser. No. 09/290,919, filing date Apr. 12, 1999, now issued as U.S. Pat. No. 6,476,604, Methods To Prevent Metal Deposited Wafers From Contaminating The Front-End Cleaning Sinks Or Front-End Furnaces, assigned to the same assignee as the present invention.

BACKGROUND OF THE INVENTION

(1) Field of the Invention

The invention relates to the field of semiconductor wafer manufacturing, and more specifically to methods of preventing partially processed wafers that have to be reworked from contamination front-end operations of the manufacturing line.

(2) Description of the Prior Art

Semiconductor wafer processing typically is a complex process including a large number and variety of processing steps. These processing steps are, during each of the sequences that are executed as part of the step, closely monitored and may result in a complex web of rework, rejects, partial rework, etc. This leads not to the ideal processing sequence where a wafer proceeds from known step to known step but can, result in many diverse flows of partially completed wafers. Wafers may be returned to prior processing steps causing concerns of wafers further down the processing line being contaminated with wafers that have already undergone more advanced steps of processing. It is therefore important to screen for such occurrences and to limit or eliminate the impact of contamination that may be introduced into a wafer processing operation by wafers that are not part of the regular wafer processing flow.

During normal wafer processing, meticulous attention is paid to obtaining and maintaining a clean and particle free environment. This clean environment has a direct impact on wafer yield and therefore on wafer cost. Wafer processing by its very nature tends to introduce impurities into the processing environment, these impurities can for instance be introduced from wafer processing furnaces. Dependent on the type of particle, these particles may diffuse into the semiconductor substrate, especially in areas of the manufacturing process where high frequency operations are being performed on the substrate. This can have a severe detrimental effect on wafer properties making these wafers unsuitable for further use. In other cases, donor or acceptor dopants may be introduced to substrates. These dopants can have a direct affect on the performance of the devices that are at a later stage to be created from these wafers. Yet other impurities can cause surface defects in the surface of the wafer or stacking faults or dislocations in the atomic structure of the substrate. Poor wafer surface can be caused by organic matter that is present in the wafer-processing environment, such as oil or oil related matter.

All of these impurities must be carefully monitored and controlled and must, when present, be removed from the wafer processing environment. This control must be exercised within the cycle of wafer processing steps and at the beginning of the wafer processing process. The frequency and, intensity of such contaminant control operations is highly cost dependent and should, wherever possible, be performed at as low a cost as can be accomplished. These methods of identification and elimination must therefore be simple but yet effective.

To start wafer processing with wafers that are free of contaminants, loose particles are typically first removed from the wafers by means of a wafer scrubbing process. In this way various dusts (atmospheric, silicon and quartz), photoresist chunks and bacteria are removed. Where very small particles are to be removed this is usually accomplished by a polishing operation.

Organic impurities such as hydrocarbons and greases are, after the cleaning process, removed with the use of solvents such as trichloroethylene, acetone, p-xylene, methanol and ethanol. A final cleaning can then be performed using various inorganic chemicals to remove heavy metals, for example. These inorganic chemical mixtures are strong oxidants, which form a thin oxide layer at the wafer surface. This oxide layer is stripped, removing impurities absorbed into the oxide layer.

Also used to further enhance wafer cleaning can be conventional chemical cleaning operations that include acid and rinse baths. These processes remove chemically bonded film from the surface of the wafer.

A further cleaning operation includes the use of mechanical scrubbing operations. These operations tend to be aggressive cleaning operations that use polishing pads affixed to turning tables that hold the substrate that is being polished. Due to the nature of this cleaning operation, the operation needs to be carefully monitored and special precaution needs to be taken to assure that particles that are removed during the operation are removed from the environment.

Typically, the turntable is rotated at various controlled speeds, for, instance 10 to 100 RPM, in a controlled clockwise or counterclockwise direction. A silicon wafer, generally in the form of a flat, circular disk, is held within a carrier assembly with the substrate wafer face to be polished facing downward. The polishing pad is typically fabricated from a polyurethane and/or polyester base material.

Another field in the high density interconnect technology is, the physical and electrical interconnection of many integrated circuit chips to a single substrate commonly referred to as a multi-chip module (MCM). A multi-layer structure is created on the substrate in order to achieve a high wiring and packing density. This multi-layer structure allows for short interconnects and improved circuit performance. Separation of the planes within the substrate, such as metal power and ground planes, is accomplished by separating the layers with a dielectric such as a polyimide. Metal conductor lines can be embedded in other dielectric layers with via openings that provide electrical connections between signal lines or to the metal power and ground planes.

In the indicated processes, great care is used to assure that the surfaces of interfaces have good planarity. In a multi-layer structure, a flat surface is extremely important to maintain uniform processing parameters from layer to layer. Layer dependent processing greatly increases processing complexity. Many approaches to producing a planar surface have been incorporated into methods of fabricating high density interconnects and integrated circuit chips in the past. For instance, the lines and vias can be planarized by applying multiple coatings of polyimide which are used to achieve an acceptable degree of planarization. Application of multiple coatings of thick polyimide is however time consuming and creates high stress on the substrate.

The problems associated with prior art polyimide processes have become more troublesome. For example, one of the main difficulties with polyimide processes is that the profiles (i.e. slopes) of the polyimide at the bonding pad edges are not consistent. Rough edges or films having numerous flakes and other defects are pervasive throughout the prior art. In other cases, pieces of photoresist can sometimes become deposited on the surface of the bonding pads causing spikes of unetched passivation layer to be left behind on the bonding pad itself. Although these problems have not prevented the use of conventional polyimide processes in conjunction with standard wire bonding techniques, these shortcomings are unacceptable in the newer, more advanced bonding.

All of the above indicated processing conditions and environments can lead to the introduction of a large number of contaminants and therefore lead to the need for strict control of the environment and the way in which the wafers that are being processed are being routed. Among the contaminants that can accumulate on the surface of a substrate are metals such as copper or aluminum. Control mechanisms that enhance the monitoring of the level of metal deposited on the surface of a wafer prevent unnecessary re-routing and rework of such wafers. Production cost of semiconductor wafers will be reduced if such wafers can be identified so that only wafers that need to be rerouted for rework are entered into the rework cycle.

U.S. Pat. No. 5,820,689 (Tseng et al.) discloses a wet chemical treatment system.

U.S. Pat. No. 5,552,327 (Bachmann et al.) shows a method for monitoring etching using reflectance spectroscopy.

U.S. Pat. No. 5,840,368 (Ohmi) shows a furnace system.

U.S. Pat. No. 5,683,180 (De Lyon et al.) shows a method of wafer temperature measurement using reflectivity spectroscopy.

U.S. Pat. No. 5,364,510 (Carpio) shows a scheme for bath chemistry control.

SUMMARY OF THE INVENTION

It is the primary objective of the invention to identify semiconductor substrates that contain metal on the surface of the substrate.

It is a further objective of the invention to inhibit incorrect routing of wafers.

It is a further objective of the invention to eliminate unnecessary substrate, rework activities.

It is a further objective of the invention to reduce the overall cost of substrate manufacturing.

It is yet another objective of the invention to reduce human error in the identifying and routing of substrates in the substrate manufacturing process.

It is yet another objective of the invention to reduce the workload for front-end cleaning sinks and furnaces.

It is yet another objective of the invention to prevent mixing of rework wafers with regular wafer processing flow.

It is yet another objective to prevent unnecessary wafer scrapping due to suspected metal contamination.

In accordance with the objectives of the invention, a new method of detecting and measuring the level of metal present on the surface of a substrate is achieved. A wafer can, at any time and at any location within the wafer processing cycle, be measured for the existence of metal on the surface of the layer, The presence of metal causes the raising of a visual or audible alarm thereby invoking human or automatic intervention.

Under the first embodiment of the invention, rf power is directed at the surface of a wafer, the reflected rf energy is captured and analyzed for intensity and frequency content. Based on this analysis conclusions can be drawn regarding presence and type of metal on the surface of the wafer.

Under the second embodiment of the invention, a source of light exposes the surface of the wafer under an angle such that part of the light reflects off this surface. The reflected light is captured and measured. Based on the measurements obtained in this manner, conclusions can be drawn concerning the reflectivity of the reflecting surface, that is the surface of the wafer. These conclusions lead directly to a measurement of the amount of metal present on the surface of the wafer.

Under the third embodiment of the invention, a magnetron radiates electromagnetic energy in the frequency range of microwave frequency. This energy is, under an angle, directed at the surface of the wafer that is being evaluated. Part of the energy is reflected by the surface of the wafer, another part passes through the wafer and can be measured after it has passed through the wafer. By comparing the level of the reflected energy with the level of the energy that passed through the wafer, conclusions can be drawn about the reflectivity of the wafer surface and therefore about the amount of metal that is present on the surface of the wafer.

DESCRIPTION OF THE PREFERRED EMBODIMENT

Figure 1:
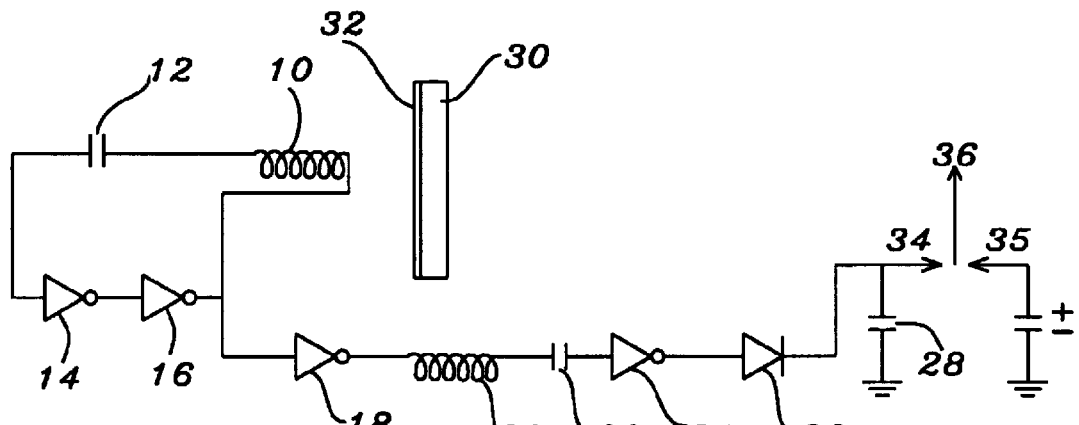
FIG. 1 shows details of the implementation of the first embodiment of the invention, which uses an rf metal detector arrangement to measure the presence of metal on the surface of a wafer.

Referring now specifically to FIG. 1, there is shown an electronic circuit that serves as a means to identify and measure the amount of rf energy that is reflected by the surface of a wafer.

The electronic circuit contains three functional sections: a LC resonating circuit, a LC tuning circuit and a rectifying circuit.

RF energy of a certain frequency is generated by an rf generating circuit that comprises the amplifiers 14 and 16 and the LC tuning components 12 and 10. The resonating rf wave is amplified by amplifier 18 and passes through the second tuning circuit consisting of inductor 20 and capacitor 22. The second tuning circuit 20/22 selects specifically the rf frequency generated by the first tuning circuit 12 and 10. The selected wave is then amplified by amplifier 24 and rectified by diode 26 and capacitor 28 to form a dc signal 34, this dc voltage 34 can be compared with a reference dc voltage 35, providing the means for compared the dc voltage 34 with the limit voltage level 35.

When a wafer with a metal layer is brought in proximity with the coil 10, the inductance and the stray capacitance of the first resonating circuit changes. The frequency generated is therefore shifted and can no longer pass through the second tuning circuit causing the dc output voltage to be reduced or to be eliminated. This triggers an alarm and produces a control signal that stops the subsequent action of putting the wafer into a cleaning sink or a furnace, thereby avoiding the contamination.

Figure 6A:
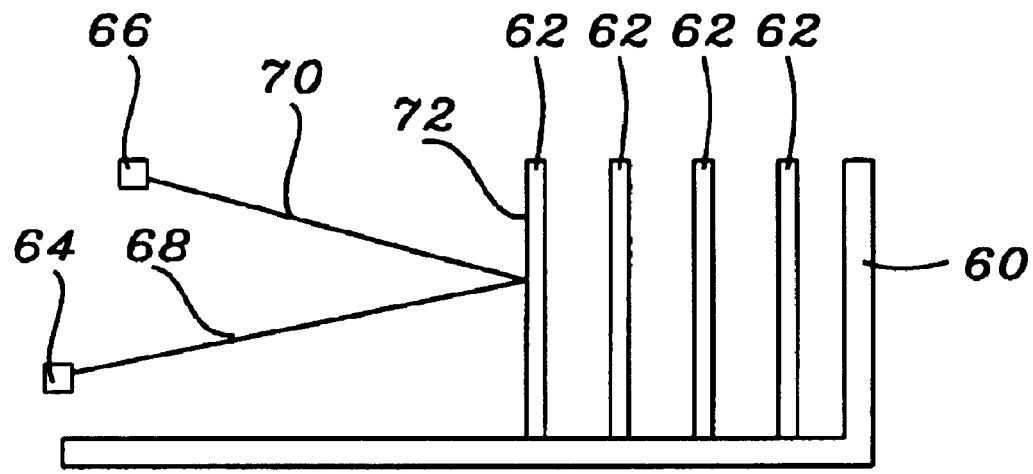
FIGS. 6a and 6b show two possible applications of the invention in re-routing wafers.
Figure 6B:
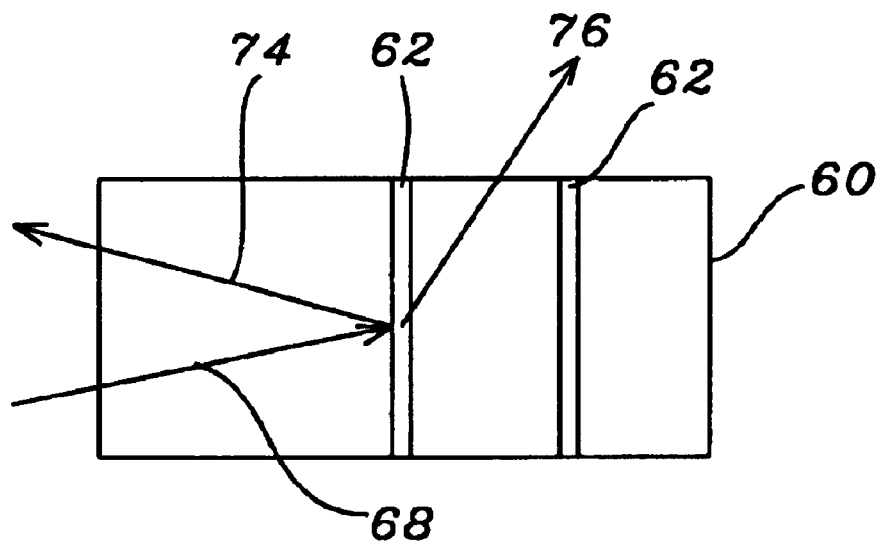

From the above provided description it is clear that the circuit arrangement that is shown in diagram form in FIG. 1 provides the means for comparing a dc voltage level 34 (which is indicative of the amount of rf energy that is reflected by the surface of a substrate) with a limit or reference voltage level 35. Based on the outcome of this compare (the dc voltage 34 can be lower than, equal to or higher than the reference or limit dc voltage 35) an alarm signal 36 can be raised in the form of a blinking light or an audible alarm for the initiation of human intervention. Alarm signal 36 can also be in the form of a voltage output that activates for instance a robotic arm (not shown in FIG. 1) that can be used to initiate machine controlled or automatic intervention by removing wafers from a wafer holder. FIGS. 6a and 6b show further examples of this latter (automated) intervention.

From the diagram that is provided in FIG. 1 the following can be summarized:

- high metal surface content can be identified on the surface of a substrate content can be identified on the energy; the source of rf energy comprises amplifiers 14, 16 and a tuning circuit comprising a capacitor 12 and an inductor 10; the rf energy that is created by the source of energy is fed into the first component 18 of the rf measurement apparatus (see following description)
- the source of rf energy provides rf energy having a frequency and an amplitude to a rf energy measurement apparatus, this rf measurement apparatus is made up of components 18 (an amplifier), 20 (an inductor), 22 (a capacitor), 24 (an amplifier), 26 (a diode) and 28 (a capacitor)
- the rf energy measurement apparatus generates a dc voltage 34 that is indicative of the frequency and the amplitude of the rf energy that is provided to the rf energy measurement apparatus by the source of rf energy
- by exposing the surface of the semiconductor substrate to the source of rf energy and by including the surface of the substrate into the tuning circuit 10/12 of the source of rf energy, the frequency of the tuning circuit 10/12 changes from a first rf energy having a first frequency and a first amplitude to a second rf energy having a second frequency and a second amplitude of the rf waves created by the source of rf energy due to metal that is present in the surface of the substrate
- by entering the second rf energy into the rf energy measurement apparatus, the rf energy measurement apparatus creates a dc voltage level that is indicative of the second rf energy
- a dc reference voltage level 35 is provided, and
- by comparing the dc voltage level 34 created by the energy measurement apparatus (which is indicative of the second rf energy) with the dc reference voltage level 35, and by determining if the dc voltage level created by the energy measurement apparatus is below or equal to the dc reference voltage level, the presence or absence of metal on the surface of the substrate can be determined.

It is well known in the art that the resonant rf energy that is created by a tuned (LC) circuit, in this case the capacitor 12 in combination with the inductor 10, creates an electromagnetic field that surrounds the tuned LC circuit. By affecting this electromagnetic field, the rf energy of the LC circuit is affected which is another way of saying that the frequency and amplitude of the rf energy can be affected by the presence or absence of an influencing source. This source is, using the invention, metal that is present on the surface of a substrate. Metal absorbs electromagnetic energy, if metal (on the surface of a substrate) is therefore positioned in close proximity to the tuned LC circuit 10/12, the rf energy that is created by this circuit is changed. It is this change in rf energy that is used by the invention to detect the presence or absence of metal on the surface of a semiconductor substrate.

It is also well known in the art that any apparatus that is used to monitor or measure an event needs, as part of these activities, to be calibrated. In the case of the rf energy measurement apparatus of the invention, this apparatus measures rf energy. The rf energy measurement apparatus must therefore be calibrated to provide a dc voltage of known value for each level of rf energy (rf frequency and rf amplitude) and for each configuration of location and orientation between the source of rf energy, that is the rf tuning circuit 10/12, and the surface of the substrate that is being evaluated for presence or absence of metal on the surface thereof.

Figure 7:
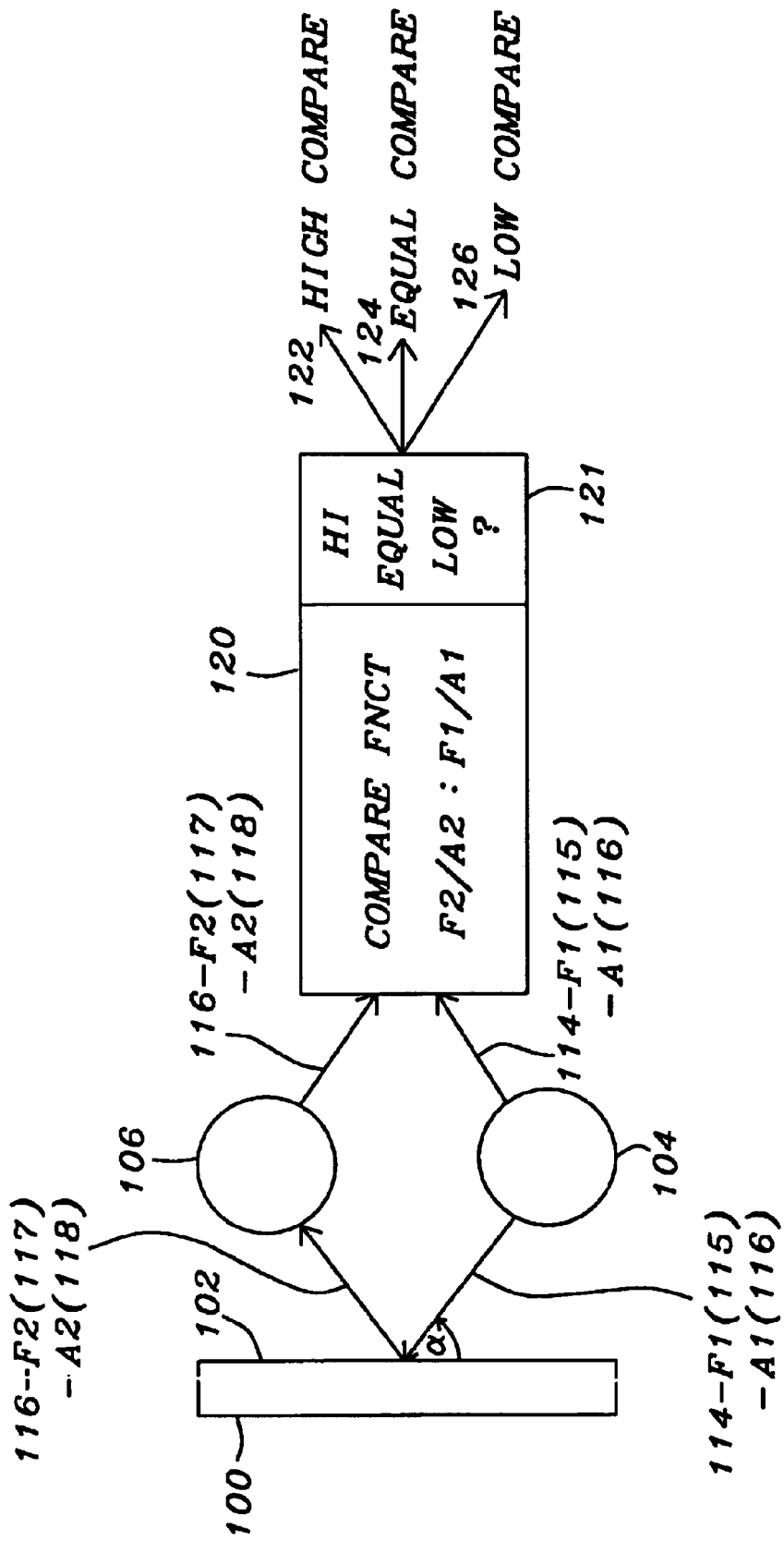
FIG. 7 shows an alternate and further detailed implementation of the invention.

The invention, which provides a method for identifying high metal surface content substrate, can alternately yet by highlighted as follows, using FIG. 7 for this purpose, as follows:

- providing a semiconductor substrate 100, the substrate 100 having a surface 102
- providing a Light Emitting Diode 104, the Light Emitting Diode 104 providing if waves having a frequency and an amplitude
- providing a light reflectivity measurement apparatus 106, the light reflectivity measurement apparatus being able to generate an indication of the frequency and the amplitude of an rf wave
- exposing the semiconductor substrate 100 to a first rf wave 114 emitted by the Light Emitting Diode 104, the first rf wave 114 comprising a first rf frequency F1 (115) and a first rf amplitude A1 (116), whereby the LED rf wave exposure 114 is under an angle α between about 30 and 60 degrees with the semiconductor substrate 110
- capturing a second rf wave 116 reflected by the semiconductor substrate 100, thereby driving the light reflectivity measurement apparatus 106, the second rf wave 116 comprising a second rf frequency F2 (117) and a second rf amplitude A2 (118)
- measuring reflectivity of the reflected rf wave 116 by comparing (function 120 shown in FIG. 7) the second rf frequency (F2, 117) and amplitude (A2, 118) with the first rf frequency (F1, 115) and amplitude (A1, 116), and
- determining (function 121 shown in FIG. 7) if the first rf frequency and amplitude compared with the second rf frequency and amplitude is within a range of values the LED 104 creates rf waves within a rf wave frequency range, the LED 104 is positioned in a stationary location with respect to the substrate 100 the light reflectivity measurement apparatus 106 is calibrated to provide a light reflectivity of known value for each of the first rf frequency F1 (115) and the first rf amplitude A1 (116) and for a physical configuration of location and orientation between the Light Emitting Diode 104 and the substrate 100 exposing the semiconductor substrate 100 to the Light Emitting Diode 104 is exposing the active side 102 of the semiconductor substrate 100 to the first rf wave 114 of the Light Emitting Diode 104 the measuring reflectivity of the reflected rf wave 116 is measuring the reflectivity of the substrate 100, thereby identifying the rf wave reflectivity in accordance with the difference between the first rf frequency (F1, 115) and amplitude (A1, 116) and the second rf frequency (F2, 117) and amplitude (A2, 118)

the determining if the first rf frequency and amplitude compared with the second rf frequency and amplitude is within a range of values (function 120, shown in FIG. 7) is determining whether the reflectivity of the reflected light is higher (122, shown in FIG. 7) than, lower than (126, shown in FIG. 7) or within a range (124, shown in FIG. 7) of reflectivity values, thereby providing an electrical signal reflecting the outcome of the determination, the electrical signal being indicative of result of the compare being either a high compare 122 or an equal compare 124 or a low compare 126.

Figures 2A, 2B:
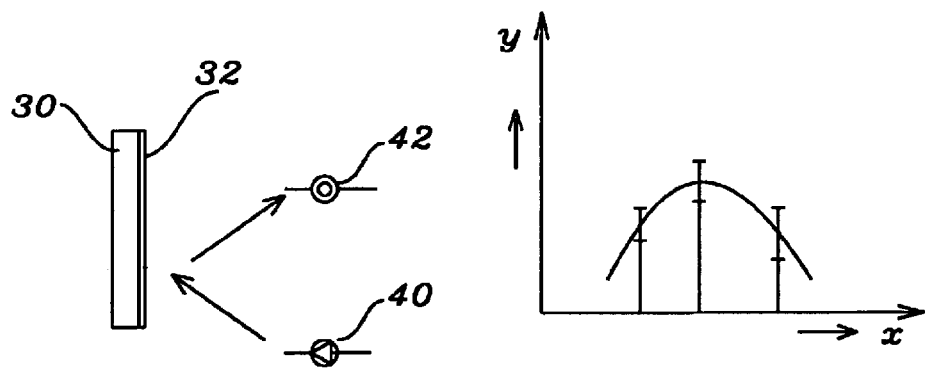
FIGS. 2a and 2b show details of the implementation of the second embodiment of the invention, which uses a light emitting diode for the source of energy that is reflected off the surface of the wafer.

FIGS. 2a and 2b show an arrangement that has the same objectives as described under FIG. 1 above. In the implementation of the invention as shown in FIG. 2a, the source of energy is a Light Emitting Diode (LED) 40. The LED shown can be selected to generate light of different wavelengths, for instance red, green and blue. The light that is reflected by the surface 32 of wafer 30 can be detected by a photodetector 42. This photodetector is also sensitive to light of a particular frequency. FIG. 2b shows a graph indicating the reflectivity of metal as a function of frequency (or wavelength) of the light that is reflected. The vertical or Y-axis shows the amount of energy that is reflected, the horizontal or X-axis shows the wavelength of the light that is reflected. The type and amount of metal that is present in a reflecting surface can be identified by the amount of energy that the surface reflects. This amount of energy is different for the frequencies or wavelengths that are contained within the light that is reflected. Visible light contains many different frequencies, in many applications red, green and blue are used for working purposes since these colors are the primary colors.

A given metal, for instance aluminum, reflects the three primary colors in a unique and identifiable way. For a particular metal, the reflectivity of each of the three primary colors is known. This means that for light of one particular frequency, for instance red, that is reflected by a known metal, for instance aluminum, the reflectivity values are known for this combination light with metal (for instance red with aluminum). From this it is clear that by measuring reflectivity of an unknown metal (the metal that must be identified) using a known light (frequency/wavelength), for instance red, and comparing this reflectivity measurement with the known (range of) reflectivity values that can be expected from various metals, the metal that fits the measured reflectivity profile can be identified.

By using the wavelengths of the three primary colors (red, green and blue) the amount of light that is reflected by the surface of the wafer (the reflectivity) by these primary colors can be measured (by the photodetector). The three primary colors have unique wavelengths, these wavelengths are indicated as three points on the X-axis of FIG. 2b. The Y-axis of FIG. 2b indicates reflectivity values. The reflectivity values (Y-axis values) measured for the three primary colors (X-axis values) can then be plotted in FIG. 2b. The range of reflectivity values (Y-axis values) is, for a particular metal, known. If therefore the three measurements of reflectivity that have been obtained in the manner indicated fall within the (known) range for a particular metal, the conclusion is clear that the metal that is present on the reflecting surface (the surface of the wafer) is the same metal as the metal that belongs to that range of reflectivity values. Therefore, in measuring the reflectivity for 3 wavelengths, for instance 300, 500 and 700 nm, and if for all three points the measured reflectivity falls within the range of for instance aluminum, the conclusion is apparent that aluminum is present on the surface of the wafer. An automatic response mechanism can be implemented to respond to the presence of aluminum on the surface of the wafer. This can be implemented by using three LED's and three photodiodes and an "and" circuit that gives a signal when the output voltage of all three diodes falls within a specific range of values.

Figure 3:
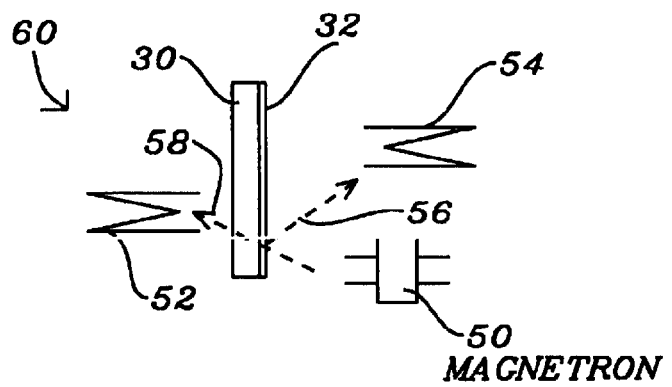
FIG. 3 shows details of the implementation of the third embodiment of the invention, which uses a magnetron for the source of energy that is reflected off the surface of the wafer.

FIG. 3 uses a magnetron 50 as its source of radiation in the range of microwave frequencies. This radiation is again aimed under an angle at the wafer that is being tested. Part 56 of the energy that strikes the surface of the wafer is reflected, part 58 of the energy penetrates the surface of the wafer and can be measured "behind" the wafer. The magnetron 50 is positioned approximately as shown with respect to the position of the wafer, microwave detector 52 measures the energy that has penetrated the wafer, microwave detector 54 measures the energy that is reflected by the surface 32 of the wafer 30. A strong reflection by the surface 32 of wafer 30 indicates the presence of metal on that surface, if therefore detector 54 measures a higher level of microwave energy than detector 52, it is clear that metal is present on the surface of the wafer. Automatic response mechanisms can be implemented that are activated either by the signal from the detector for reflection or by the detector for transmission or by subtracting the signal of one from the other.

Highlighted in FIG. 3 is a means 60 for initiating intervention if the reflected microwave energy 56 exceeds the passed through microwave energy 58. This intervention can be intervention by a human operator or can be an intervention that is controlled by a semiconductor processing tool.

Figure 4:
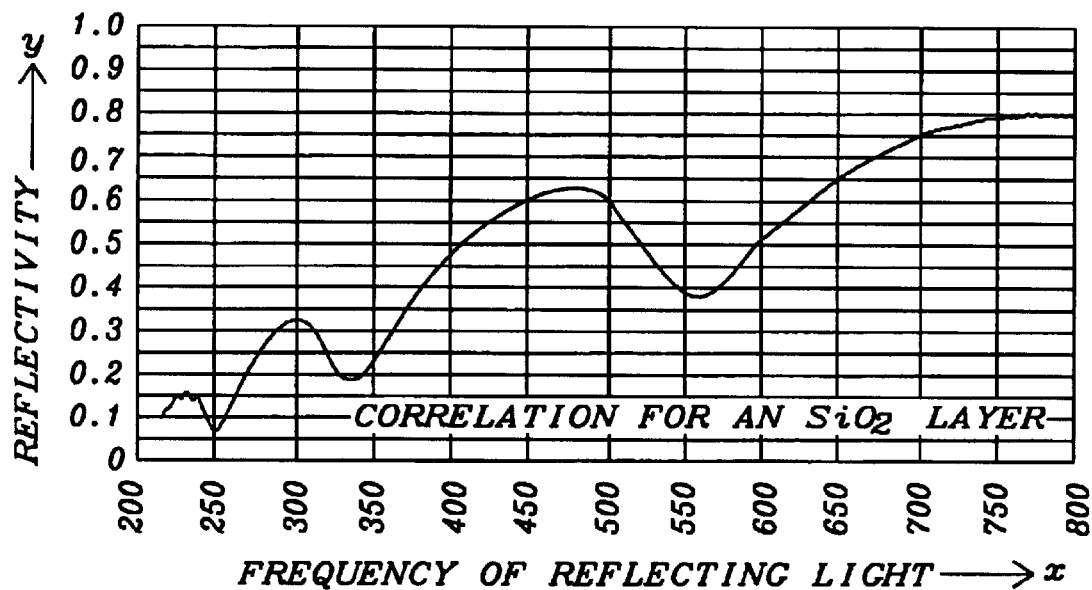
FIG. 4 shows a graph of the reflectivity of a $SiO_2$ layer deposited on Si as a function of wavelength.
Figure 5:
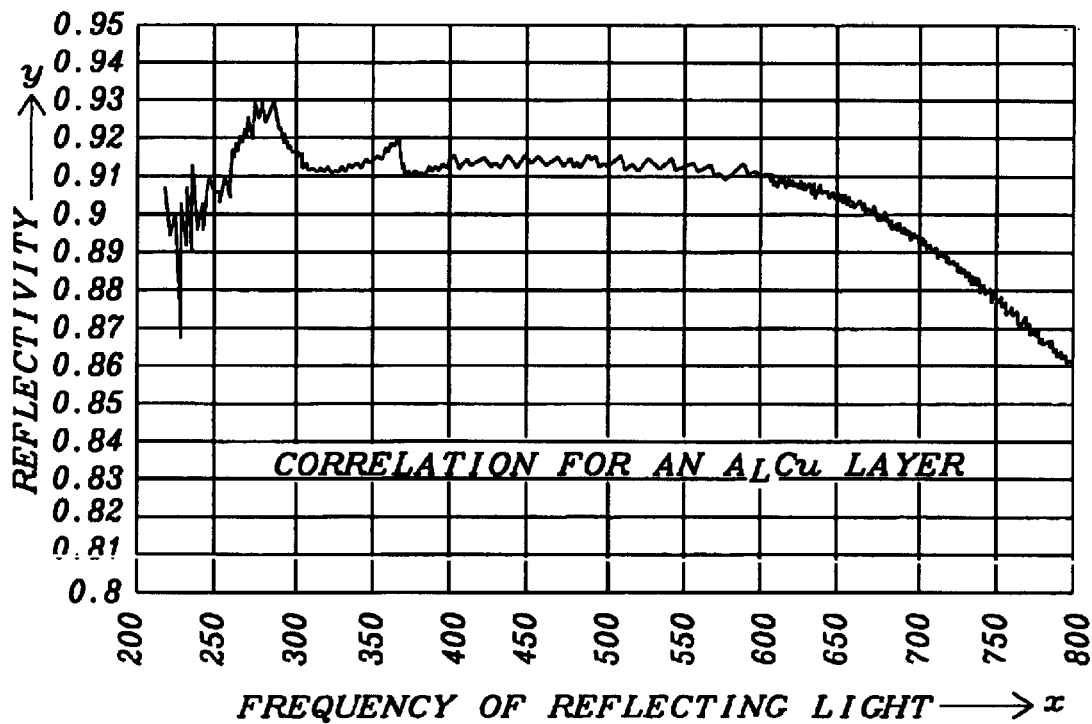
FIG. 5 shows a graph of the reflectivity of a layer of AlCu as a function of wavelength.

FIGS. 4 and 5 further emphasize the basic concept underlying the invention, that is that surface reflectivity is dependent on the type and concentration of the material contained within the reflecting surface and is dependent on the frequency of the wavelength of the energy that is reflected from this surface. Both FIG. 4 and FIG. 5 show the different reflectivity optical light of an $SiO_2$ surface as compared with an aluminum surface. FIG. 4 shows this correlation for a layer of $SiO_2$ that has been deposited on the surface of a layer of Si. FIG. 5 shows this correlation for a layer of AlCu that has been deposited on the surface of a layer of Si. FIGS. 4 and 5 apply to the LED—photodiode method only. It is clear that both correlations have very unique and identifiable characteristics, these characteristics are used as the basis for the invention. Most noteworthy in FIG. 4 is the seesaw nature of the reflectivity of the $SiO_2$ layer as the frequency of the reflected light decreases. FIG. 5 shows that, for AlCu, the reflectivity is and remains at a plateau from where the reflectivity only slowly decreases for relatively high frequencies in the reflected light.

FIG. 6a shows a side view of an implementation of the invention that lends itself to automatic handling of wafers based on the amount and type of metal on the surface of the wafer. The metal detector apparatus as described can be mounted as shown, facing the surface of the wafers and linked to a robotic arm that can be used to remove wafers from the teflon wafer holder. The action of removal is triggered by the level of detection reaching a level that indicates the presence of metal, the robotic arm removes the wafer in question and positions that wafer into another wafer carrier for further wafer processing. The operation of identifying contaminated (with metal) wafers is thereby automated and removed from human intervention and human error. Wafers 62 are mounted in the wafer carrier 60, the source of energy 64 broadcasts the energy 68 to the surface 72 of the wafer 62, part 70 of the energy is reflected by the surface 72 and detected by the energy detector 66. This energy detector can readily determine the presence and type of metal, if any, which is present on the surface 72 of wafer 62.

FIG. 6b shows a top view of a similar arrangement that allows the application of using a magnetron as source of energy whereby the incident radiated energy 68 is partially reflected (74) by the surface of the wafer 62 and partially transverses (76) the wafer. Wafers 62 are mounted in the wafer carrier 60. By measuring and, comparing the reflected energy 74 with the penetrated energy 76, conclusions can be drawn regarding the presence and type on metal on the surface of the wafer.

For the applications of the invention as shown in FIGS. 6a and 6b, methods known in the art of wafer processing and wafer handling can be applied for removing wafers that have undesirable surface coatings of metal. These wafers, once removed from the normal wafer processing flow, can then be handled in accordance with required procedures established for such wafers.

Although the present invention is illustrated and described herein as embodied in the construction of a number of examples, it is nevertheless not intended to be limited to the details as presented. Rather, various modifications may be made in the details within the scope and range of equivalents of the claims and without departing from the spirit of the invention.

What is claimed is:

1. A method for identifying high metal surface content substrate comprising:

providing a semiconductor substrate, said substrate having a surface;

providing a Light Emitting Diode, said Light Emitting Diode providing rf waves having a frequency and an amplitude;

providing a light reflectivity measurement apparatus, said light reflectivity measurement apparatus being able to generate an indication of the frequency and the amplitude of rf waves;

exposing said semiconductor substrate to a first rf wave emitted by said Light Emitting Diode, said first rf wave comprising a first rf frequency and a first rf amplitude, whereby said LED rf wave exposure is under an angle between about 30 and 60 degrees with said semiconductor substrate;

capturing a second rf wave reflected by said semiconductor substrate, thereby driving said light reflectivity measurement apparatus, said second rf wave comprising a second rf frequency and a second rf amplitude;

measuring reflectivity of said reflected rf wave by comparing said second rf frequency and amplitude with said first rf frequency and amplitude; and determining if said first rf frequency and amplitude compared with said second rf frequency and amplitude is within a range of values.

2. The method of claim 1 whereby providing a Light Emitting Diode (LED) is providing a LED that creates rf waves within a rf waves frequency range, whereby furthermore said LED is positioned in a stationary location with respect to said substrate.

3. The method of claim 1 whereby said light is red light followed by green light followed by blue light.

4. The method of claim 1, wherein said light reflectivity measurement apparatus measures frequency and amplitude of rf waves, whereby said light reflectivity measurement apparatus is calibrated to provide a light reflectivity of known value for each of said first rf frequency and said first rf amplitude and for a physical configuration of location and orientation between said Light Emitting Diode and said substrate.

5. The method of claim 1 whereby said exposing said semiconductor substrate to said Light Emitting Diode is exposing the active side of said semiconductor substrate to said first rf wave of said Light Emitting Diode.

6. The method of claim 1 wherein said measuring reflectivity of said reflected rf wave is measuring the reflectivity of said substrate, thereby identifying said rf wave reflectivity in accordance with the difference between said first rf frequency and amplitude and said second rf frequency and amplitude.

7. The method of claim 1 wherein said determining if said first rf energy frequency and amplitude minus said second rf frequency and amplitude is within a range of values is determining whether said reflectivity of said reflected light is higher than, lower than or within a range of reflectivity values, thereby providing an electrical signal reflecting the outcome of said determination, said electrical signal being indicative of result of said compare being either a high compare or an equal compare or a low compare.

8. An apparatus for identifying high metal surface content substrate comprising:

a Light Emitting Diode, said Light Emitting Diode providing rf energy comprising rf waves having a frequency and an amplitude;

a rf wave reflectivity measurement apparatus, said light reflectivity apparatus being able to generate a value being indicative of the frequency and amplitude of rid rf wave;

a means for setting a first rf wave emitted by said Light Emitting Diode to a first rf frequency and amplitude;

a means for exposing a semiconductor substrate to the first rf wave emitted by said Light Emitting Diode, said LED rf wave exposure being under an angle between about 30 and 60 degrees with said semiconductor substrate;

a means for capturing a second rf wave reflected by said surface of said semiconductor substrate, driving said light reflectivity measurement apparatus;

a means for measuring the reflectivity of said reflected second rf wave by subtracting said second rf frequency and amplitude from said first rf frequency and amplitude; and a means for determining if said first rf frequency and amplitude compared with said second rf frequency and amplitude is within a range of values.

9. The apparatus of claim 8, whereby a Light Emitting Diode (LED) is a LED that creates rf waves within a rf waves frequency range, whereby said LED is positioned in a stationary location with respect to said substrate.

10. The apparatus of claim 8 whereby said light is red light followed by green light followed by blue light.

11. The apparatus of claim 8 wherein said light reflectivity measurement apparatus measures frequency and amplitude of rf waves, whereby said light reflectivity measurement apparatus is calibrated to provide a reflectivity of known value for each first and second rf frequency and amplitude and for each configuration of location and orientation between said Light Emitting diode and said substrate.

12. The apparatus of claim 8 whereby said means for exposing said semiconductor substrate to said Light Emitting Diode is exposing the active side of said semiconductor substrate to said Light Emitting Diode.

13. The apparatus of claim 8 wherein said means for measuring said reflected light energy is measuring the reflectivity of said first rf wave, thereby determining a metal content on a substrate.

14. The apparatus of claim 8 wherein said comparing said second rf frequency and amplitude with said first rf frequency and amplitude is determining whether said reflectivity of said reflected light is higher than, lower than or within a range of reflectivity values, thereby providing an electrical signal reflecting the outcome of said subtraction, said electrical signal being indicative of the result of said subtraction being either a high compare or an equal compare or a low compare.

* * * * *